US011706604B2

(12) United States Patent
Wirth et al.

(10) Patent No.: US 11,706,604 B2
(45) Date of Patent: Jul. 18, 2023

(54) RESPONDING TO EMERGENCY CALLS

(71) Applicant: KONINKLIJKE PHILIPS N.V., Eindhoven (NL)

(72) Inventors: Christoph Tobias Wirth, Vellmar (DE); Jorn Op Den Buijs, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/462,443

(22) Filed: Aug. 31, 2021

(65) Prior Publication Data
US 2022/0070646 A1 Mar. 3, 2022

(30) Foreign Application Priority Data
Sep. 2, 2020 (EP) .................................... 20194177

(51) Int. Cl.
H04W 4/90 (2018.01)
G16H 10/60 (2018.01)
G08B 21/02 (2006.01)
G10L 17/06 (2013.01)

(52) U.S. Cl.
CPC .............. H04W 4/90 (2018.02); G08B 21/02 (2013.01); G10L 17/06 (2013.01); G16H 10/60 (2018.01)

(58) Field of Classification Search
CPC ........ G16H 10/60; G08B 21/02; G10L 17/06; H04W 4/90
USPC ..................................... 455/404.01
See application file for complete search history.

(56) References Cited

U.S. PATENT DOCUMENTS

| 2009/0216534 | A1* | 8/2009 | Somasundaram | ..... G16H 40/20 705/28 |
| 2010/0130161 | A1 | 5/2010 | Rieth | |
| 2010/0267361 | A1* | 10/2010 | Sullivan | .................. G01S 19/17 455/404.2 |
| 2014/0370841 | A1* | 12/2014 | Roberts | ................... H04W 4/90 455/563 |
| 2018/0322961 | A1* | 11/2018 | Kim | ....................... G16H 80/00 |
| 2019/0069145 | A1 | 2/2019 | Dantsker | |

(Continued)

FOREIGN PATENT DOCUMENTS

WO 2020011244 A1 1/2020

OTHER PUBLICATIONS

Blomberg, S. et al., "Machine learning as a supportive tool to recognize cardiac arrest in emergency calls", Resuscitation, vol. 138, May 2019, pp. 322-329.

(Continued)

Primary Examiner — Maria El-Zoobi

(57) ABSTRACT

According to an aspect, there is provided an apparatus (500; FIG. 5) for determining an action to be taken in response to an emergency call, the apparatus comprising: a processor (502; FIG. 5) configured to receive an indication that an emergency call has been initiated; extract, from speech transmitted as part of the emergency call, features indicative of a medical condition or event relating to a subject; obtain medical data relating to the subject; predict, based on the extracted features and the medical data, an acuity level of the subject; determine, based on the acuity level, an action to be taken in respect of the subject; and provide an indication of the determined action for presentation to a recipient.

15 Claims, 4 Drawing Sheets

(56) References Cited

U.S. PATENT DOCUMENTS

2019/0122532 A1  4/2019  Nassabi
2020/0005188 A1  1/2020  Dugas

OTHER PUBLICATIONS

"Sonde", https://www.sondehealth.com/, Accessed on Aug. 27, 2021.
International Search Report for PCT/EP2021/073553 filed Aug. 26, 2021.

* cited by examiner

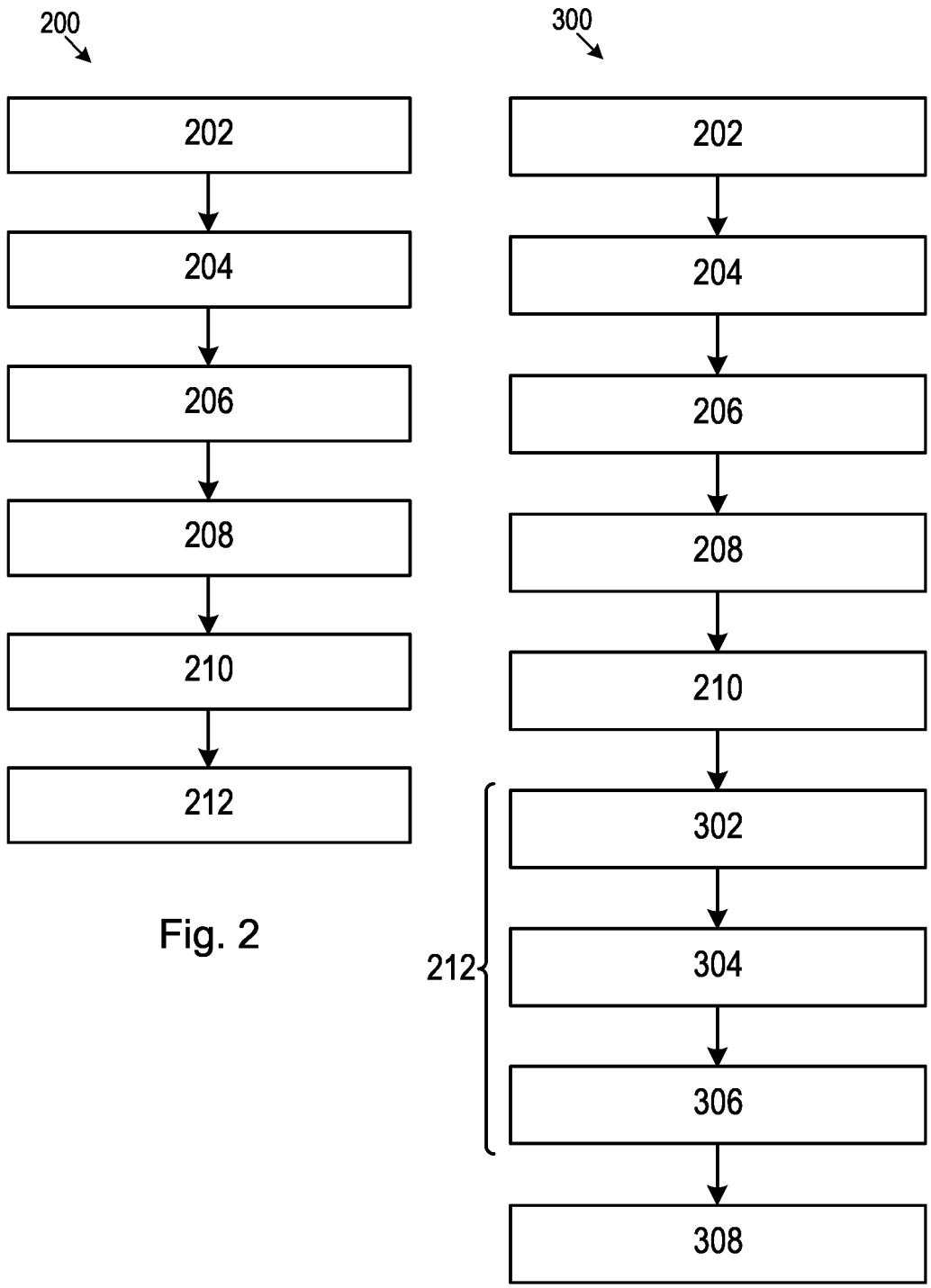

RESPONDING TO EMERGENCY CALLS

CROSS-REFERENCE TO PRIOR APPLICATIONS

This application claims the benefit of European Patent Application No. 20194177.0, filed on 2 Sep. 2020. This application is hereby incorporated by reference herein.

FIELD OF THE INVENTION

The invention relates to emergency calls and, more particularly, to determining an action to be taken in response to an emergency call.

BACKGROUND OF THE INVENTION

When an emergency call is made (e.g. by dialling 999 in the UK or 911 in the US), it is typically received by an emergency medical dispatcher who makes an assessment of the patient based on the information available to them during the call. Typically, this information may be just subjective information provided by the person making the emergency call, and the emergency medical dispatcher may have relatively little information on which to base their decision. The emergency medical dispatcher may decide whether or not to dispatch an emergency response vehicle, such as an ambulance, to attend the patient. Once the emergency response team has arrived and assessed the patient, they may make a decision regarding whether or not the patient is to be transported to a medical facility. Once that decision has been made, there may be no further assessment that leads to a change in the decision to take the patient to a medical facility, even though more information regarding the patient may have become available.

Some healthcare payment models require an emergency response service provider to transport a patient to a medical facility that is covered under its regulations, such as emergency departments at hospitals, critical access hospitals, skilled nursing facilities or dialysis centres to qualify for reimbursement. Therefore, in some cases, patients may be transported to one of these facilities to ensure that payment is received, even though a different facility (e.g. a primary care doctor's office or an urgent care clinic) or even a treatment at the scene may more appropriately meet the patient's needs. Thus, patients or insurance companies may pay more than necessary for the patient's treatment, and emergency response resources may be used unnecessarily when they could be needed elsewhere.

Therefore, there is a desire for an improved emergency response mechanism which can allocate emergency response resources more appropriately and improve the patient experience.

SUMMARY OF THE INVENTION

In order to handle emergency calls more effectively and appropriately, decisions regarding a response to an emergency call may be made making use of more available information and data. Furthermore, the assessment of the needs of the patient, sometimes referred to as "triaging" made by the emergency medical dispatcher may change over time so it may be useful to perform such a triage at multiple instances, rather than just during the emergency call. The inventors of this disclosure have recognised that such improvements may be made by using a system that assesses available information as it becomes available or changes. Moreover, the system disclosed herein is capable of assessing the information and triaging the patient in an automated manner which does not necessarily require any input from an emergency medical dispatcher, thereby freeing up their time for other higher acuity cases.

According to a first specific aspect, there is provided a computer-implemented method for determining an action to be taken in response to an emergency call, the method comprising determining that an emergency call has been initiated; extracting, from speech transmitted as part of the emergency call, features indicative of a medical condition or event relating to a subject; obtaining medical data relating to the subject; predicting, based on the extracted features and the medical data, an acuity level of the subject; determining, based on the acuity level, an action to be taken in respect of the subject; and providing an indication of the determined action for presentation to a recipient.

In some embodiments, determining an action to be taken may comprise determining, at a first time, a first action to be taken in respect of the subject; and determining, at a second time, later than the first time, a second action to be taken in respect of the subject. In an example, the first action may comprise dispatching an emergency responder to attend the subject. In an example, the second action may comprise transporting the subject to a medical facility. In some example, determining the second action to be taken may comprise determining a medical facility to which the subject is to be transported. Determining an action to be taken may further comprise determining, at a third time, later than the second time, a third action to be taken in respect of the subject.

In some embodiments, the method may comprise receiving sensor data relating to health measurements acquired in respect of the subject. Predicting an acuity level of the subject and determining an action to be taken in respect of the subject may be based on the received sensor data.

Providing an indication of the determined action for presentation to a recipient may, in some embodiments, comprise securely transmitting the indication of the determined action to the recipient, along with at least one of: data relating to the emergency call, the features extracted from the speech, at least a portion of the medical data relating to the subject, and the predicted acuity level.

In some embodiments, at least one of predicting an acuity level of the subject and determining an action to be taken in respect of the subject may be performed using a trained predictive model.

The action to be taken in respect of the subject may comprise at least one action selected from a group comprising: transporting the subject to an emergency department; providing self-care instructions to the subject without dispatching transportation; providing treatment of the subject at the scene; transporting the subject to an appropriate healthcare provider; referring the subject to an appropriate community service; providing a specific treatment or transport protocol; dispatching an ambulance to take the subject to an emergency care facility; dispatching an ambulance to take the subject to a non-emergency care facility; dispatching a non-emergency vehicle to the subject; and contacting a caregiver for the subject.

According to a second specific aspect, there is provided a computer program product comprising a non-transitory computer-readable medium, the computer-readable medium having computer-readable code embodied therein, the computer-readable code being configured such that, on execution by a suitable computer or processor, the computer or processor is caused to perform steps of the method disclosed herein.

According to a third specific aspect, there is provided an apparatus for determining an action to be taken in response to an emergency call, the apparatus comprising a processor configured to receive an indication that an emergency call has been initiated; extract, from speech transmitted as part of the emergency call, features indicative of a medical condition or event relating to a subject; obtain medical data relating to the subject; predict, based on the extracted features and the medical data, an acuity level of the subject; determine, based on the acuity level, an action to be taken in respect of the subject; and provide an indication of the determined action for presentation to a recipient.

In some embodiments, the apparatus may further comprise a call initiation unit for enabling an emergency call between a caller and a call receiver to be initiated.

The apparatus may, in some embodiments, further comprise a memory configured to store at least one of: a health record relating to the subject; a predictive model for predicting the acuity level; a predictive model for determining an action to be taken in respect of the subject; and a predictive model for predicting the acuity level and for determining an action to be taken in respect of the subject.

According to a fourth specific aspect, there is provided a system for determining an action to be taken in response to an emergency call. The system comprises a call detection module for detecting the initiation of an emergency call; a speech processing module for extracting, from speech transmitted as part of the emergency call, features indicative of a medical condition or event relating to a subject; an extraction module for extracting, from a memory, medical data relating to the subject; at least one prediction module for: predicting, based on the extracted features and the medical data, an acuity level of the subject; and determining, based on the acuity level, an action to be taken in respect of the subject; and a user interface for presenting an indication of the determined action.

The system may further comprise a call initiation module for enabling the emergency call to be initiated.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which:

FIG. 2 is a flowchart of an example of a method for responding to emergency calls;

FIG. 3 is a flowchart of a further example of a method for responding to emergency calls;

DETAILED DESCRIPTION OF EMBODIMENTS

Embodiments of the present disclosure relate generally to determining an action to be taken in response to an emergency call. The determination of the action to be taken may be based on an assessment of the acuity level of a patient in respect of whom the emergency call has been made. The acuity level may be considered to relate to a severity of the patient's situation, wound or illness. For example, a patient who has fallen and twisted their ankle may be considered to have a low acuity level while a patient who has suffered a heart attack may be considered to have a very high acuity level. The decision regarding how to respond to the emergency call may be based on the acuity level of the patient. For example, for the patient who has suffered a heart attack, an emergency ambulance may be dispatched in order to get the patient to an accident and emergency department of a hospital as quickly as possible while, for the patient with a twisted ankle, a lower-priority medical response team may be dispatched, or the patient may even be advised to travel to a walk-in clinic themselves.

The acuity level of a patient may be determined based on information provided during the emergency call, such as a description of the illness or injury suffered by the patient, a description of the patient themselves, and any other relevant information that may be available. In existing emergency response systems, an emergency response dispatcher receiving the emergency call may perform a triage of the patient based on the available information, and estimate an acuity level of patient. According to the present invention, however, information made available during the emergency call is used in addition to other information that can be obtained, and an acuity level of the patient is estimated using one number of processing techniques. Based on the estimated acuity level, a determination may be made regarding an action to be taken in respect of the patient.

Figure 1:
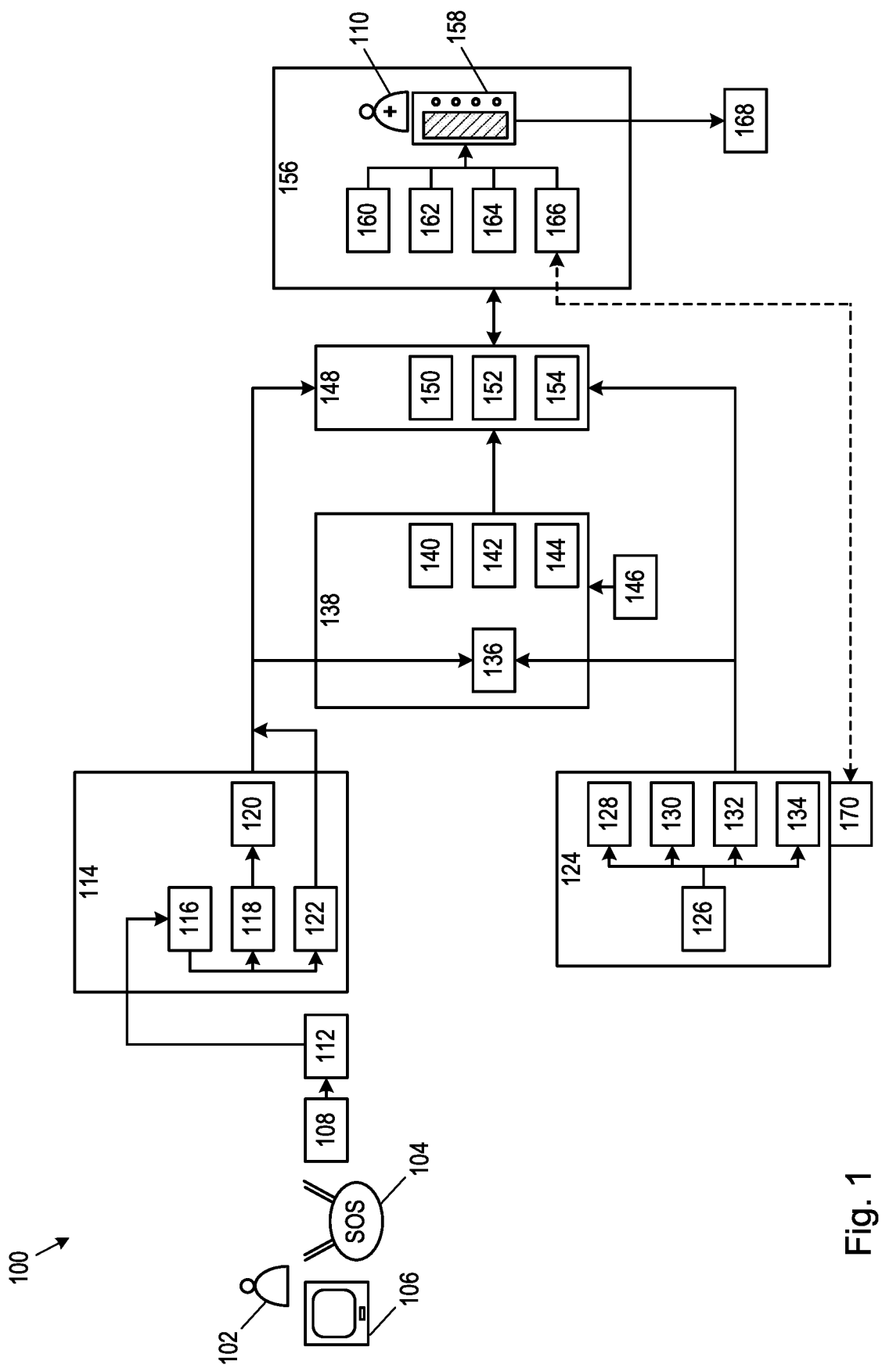
FIG. 1 is a schematic illustration of an example of a system for handling emergency calls.

Referring to the drawings, FIG. 1 is a schematic illustration of an example of an emergency call handling system 100. In this example, an emergency call is made in respect of a patient 102. The emergency call may be made by the patient 102 themselves or by another person on the half of the patient. In some examples, the patient 102 may wear an emergency communication device 104 about their person, the device having a call or SOS button which the patient can press in an emergency in order to call for assistance. Alternatively, the emergency call may be made using a computing device 106, such as a smartphone, which may include an application or a computer program capable of implementing the present invention.

The emergency call is initiated at block 108, and the patient 102 or the caller is able to communicate with call receiver, such as an emergency response dispatcher 110. In some embodiments, the emergency call may be made to the public emergency services while, in other embodiments, the call may be made as part of a private emergency response system, such as a Personal Emergency Response System (PERS). While the triaging and determination of action to be taken may be performed automatically, as described below, the skills of the emergency response dispatcher 110 may enable them to provide immediate remote assistance or advice to the patient 102 and to ask appropriate questions in order to obtain relevant information can be used when determining the action to be taken. Upon initiation of the emergency call, a call detection module 112 may detect that the call has been initiated or may receive notification of the call initiation.

During the call, call data (e.g. audio data and/or video data) including speech, sounds and video (if available), is provided to a speech processing unit or module 114 so that information can be extracted from the words and sounds made by the caller and the call receiver. In some examples, the speech processing module 114 may comprise or include a natural language processing (NLP) module or submodule. The speech processing module 114 provides audio/video input functionality in the form of an audio/video input unit or submodule 116 for receiving or extracting audio and/or video data from the call. The audio/video data (i.e. call data) may be provided to a call transcription unit or submodule 118 which may use speech recognition techniques to transcribe the call (e.g. the speech from both parties of the call). For example, a speech-to-text component may be used to transcribe the call. The transcription of the call may be provided to a word embedding unit or submodule 120 (sometimes referred to as a word embedding machine) which performs a vectorisation of words and terms used in the conversation and performs a dimension reduction in order to identify clusters of terms, words and phrases that are similar or that have a similar meaning.

In some embodiments, the speech processing module 114 may include an audio feature extraction unit or submodule 122 to extract audio features from the call. For example, the audio feature extracting submodule 122 may identify and extract vocal biomarkers that occur in the call that are relevant to disease and/or emotion. In particular, physical and perceptual domain features can be extracted using techniques that will be familiar to those skilled in the art; for example, one or more of a time domain feature, a wavelet or frequency domain feature, a multiscale spectro-temporal domain feature, a cepstral domain feature and an image domain feature may be extracted from the call data. A time domain feature may, for example, comprise a feature directly extracted from the audio data or sound waveform/signal, such as the magnitude of the signal. A wavelet feature may comprise a feature extracted after processing the audio data by wavelet transformation, which is a projection of the signal onto a set of basis functions named wavelets. Wavelet transforms can be of particular use to extract features related to crackle and wheeze-like sounds. Features can also be derived from the frequency domain, after mapping the time-domain signal into the frequency domain using e.g., the fast Fourier transform (FFT). Since frequency domain features will vary over time, of particular use are features from the spectro-temporal domain, where the FFT is computed in short (overlapping) time-windows. This can be done using multiple scales of the time and frequency resolution (multi-scale). The cepstral domain is a further transformation of the frequency domain, specifically focused on detection of echoes, reflections and other periodic structures in the frequency domain. An image domain feature can be derived after transforming the time-domain wave form into spectrogram. A spectrogram looks like an image and specific sounds (e.g. bird chirps) show a particular "fingerprint" in such images. Thus, audio feature extraction techniques are applied to machine learning for the detection, identification, classification, indexing or recognition of acoustic events occurring during the call and present in the audio data. The dynamic variations of audio signals may be analysed in one or more of the time, frequency, wavelet, image-based, cepstral, or other transformed domains and audio feature extraction techniques may be classified into the aforementioned domains. Features extracted from the call data by the feature extracting submodule 122 may be used to glean further information about the patient 102 and/or the patient's situation in order to make a more appropriate assessment of the patient's acuity level and a more appropriate determination of the action to be taken.

While the call data itself can provide substantial information about the patient 102 and their condition, embodiments of the present invention make use of additional information relating to the patient 102. The system 100 includes an extraction module 124, which may be referred to as a health record data extraction unit or module, and which is configured to retrieve or extract relevant data from health records associated with the patient 102. For example, electronic health records (e.g. EHRs), or data from such records, may be stored securely in a storage module or memory. The stored data may comprise a local or partial instance of the full EHR, and may include particular information relating to the subject to be used in the system. In other words, the subject's full EHR accessible to a medical professional may include more information and more detail than the local instance of the EHR that is available to the subject and stored locally. The health record data extraction module 124 accesses, at block 126, the memory and extracts or obtains relevant information and data relating to the patient 102 and their health including, for example, information stored under DICOM headings, past and/or recent medical history data, patient data such as their age, gender, blood type, and the like, historic healthcare utilisation data including, for example, the number of previous emergency calls made, a number of previous emergency department visits, the number of avoidable emergency department visits, the number of emergency department visits that could have been treated by a primary care physician and the number of emergency department admissions. More specifically, data may be extracted from the patient's health records indicative of medical conditions 128 from which the patient 102 is currently suffering, medical events relating to the patient 102, prescription drugs 130 that the patient is or should be taking, recent or current vital signs measurements 132 including, for example, heart rate measurements, glucose levels, blood pressure measurements and so on, and details of past clinical visits 134. In some cases, health data and/or vital signs measurements 132 may be updated and provided in real time. For example, a heart rate monitor may be worn by the patient 102, and/or other devices may be used to record other physiologic parameters including, for example, weight, blood pressure, pulse oximetry measurements and respiratory flow rate measurements.

In examples where the emergency call is made using a computing device (e.g. a smartphone) 106, then the memory storing the patient's health records may comprise or form part of the memory of the computing device itself. In other embodiments, such as where the emergency call is initiated or made using an emergency call button 104, then the health record data may be stored in a locally-accessible memory, such as a memory of a device belonging to the patient 102 and/or located at the patient's home. In some examples, personal health data relating to the patient 102 may be stored in the memory of the device when the device is connected to an electronic health record system of the healthcare organisation with whom the patient is registered. This way, data can be updated remotely, via a secure connection with the healthcare organisation, or whenever the patient visits the healthcare organisation or when a medical professional from the organisation visits patient. Alternatively, an authorised user (e.g. a medical professional) may update health data stored in the device manually. An advantage of such health data being stored locally in a device that is to perform the processing of the data, or accessible via a local network, is that the risk of a security breach (e.g. unauthorised access of personal health record data) can be reduced.

Outputs from the speech processing module 114 and the health record data extraction module 124 are provided to a data aggregation module 136 of a prediction module 138.

The prediction module 138, which may be referred to as a triaging module, is configured to predict, estimate or determine an acuity level 140 of the patient based on the data provided to the data aggregation module 136. For example, based on words, terms and phrases recognised from the transcript of the emergency call, along with audio features extracted from the call data (where available) and data acquired from the patient's electronic health record, the prediction module 138 may output a prediction that the patient's current condition is extremely severe and life-threatening, equating to a high acuity level. In contrast, if the combination of call data and data from the patient's electronic health record indicates that the patient is not in a life-threatening condition, with a low risk of their health deteriorating rapidly, then the prediction module 138 may output a low acuity level prediction. The prediction module 138 is further configured to determine, based on the acuity level, an action to be taken in respect of the patient 102. The action to be taken may include a determination or recommendation of a service 142 (e.g. dispatch an emergency ambulance, dispatch a non-emergency healthcare professional, provide over-the-phone advice) to be provided for the patient 102, and a determination or recommendation of a treatment location 144 (e.g. a hospital emergency department, a doctors' surgery, a walk-in clinic, or the like). In making the determination of the service 142 and the determination of the treatment location 144, the prediction module 138 may obtain information and data from one or more data sources 146 containing information about the proximity and availability of different medical centres and treatment locations. The prediction module 138 may, in some embodiments, comprise, or make use of, one or more trained machine learning models. Any appropriate machine learning techniques may be implemented, including for example artificial neural networks, deep neural networks, regression trees, classifiers, and the like. As described in greater detail below, the machine learning models may be trained using previously-made emergency calls for which the chosen acuity level and course of action is known.

The outputs of the prediction module (i.e. the predicted acuity level, the recommendation of the service 142 and the recommendation of the treatment location 144) are provided to a secure transfer module 148 for communication. Outputs from the speech processing module 114 and the health record data extraction module 124 may also be provided to the secure transfer module 148 for communication. The secure transfer module 148 may include various communication mechanisms or channels, including an audio channel 150, a video channel 152 and a data channel 154. The audio channel 150 is configured for communicating audio data (e.g. a portion or all of the audio data from the emergency call), and the video channel 152 is configured for communicating image or video data (e.g. a portion or of the video data from the emergency call if a video call was made). The data channel 154 is configured for communicating any other data (i.e. other than audio and video data) including, for example, the outputs of the election module and any relevant data extracted from the health record data extraction module 124.

Various security protocols may be implemented to secure the data to be transmitted using the secure transfer module 148. For example, one or more data encryption techniques may be used. In some examples, data may be transferred using a data blockchain. A secure connection may be established between the secure transfer module 148 and a display module 156 capable of presenting information to the emergency medical dispatcher 110, an ambulance medical team, healthcare providers and/or other individuals or facilities involved in providing treatment and making decisions regarding the treatment of patients. The display module 156 may be configured to present formation to a recipient via a user interface 158. Specifically, the display module 156 may be configured to present a call summary 160, summarising important points from the emergency call. The display module 156 may also be configured to present a call classification 162, including outputs of the prediction module 138, such as the predicted acuity level 140, the recommended service 142 and the recommended treatment location 144. The display module 156 may also be configured to present health data 164 acquired from the health record data extraction module 124, such as previous health conditions of the patient 102, details of medication currently being prescribed to and taken by the patient, and previous emergency call events. The display module 156 may also be configured to present vital signs measurements 166 of patient 102. The vital signs measurements 166 to be presented by the display module 156 may include the most recently acquired measurements and/or real-time measurements if available. For example, data from measurement devices (e.g. wearable devices) worn by the patient 102 may be transmitted (e.g. via the secure transfer module 148) to the display module 156 in real time.

Once a determination has been made as to the action to be taken in respect of the patient 102, any relevant parties 168 who will be affected by the decisions made can be notified. For example, if it is determined that an emergency ambulance is to be dispatched to attend the patient 102, then some or all of the data and information received by the display module 156 may be transmitted to the emergency ambulance team. Similarly, if it is determined that the patient 102 is to be transported to an emergency department of a local hospital, then the information can be transmitted to the hospital so that they are aware of the incoming patient and can make appropriate arrangements. In other examples, it may be determined that, rather than an emergency response vehicle attending the patient, an alternative transport service should be used such as a taxi or an informal caregiver, such as a relative of the patient or a nominated person indicated by the patient during an enrolment process, for example. In these examples, some of the data received by the display module 156 (e.g. the patient's name and address) may be transmitted for presentation to the relevant party 168.

In some embodiments, a person or team attending the patient 102 in response to the emergency call may take clinical measurements 170 (e.g. vital signs measurements) in respect of the patient, and these may be added to the patient's electronic health record. The up-to-date clinical measurements 170 may be extracted from personal health data stored in the patient's electronic health record (block 132) and/or presented by the display module 156 on the user interface 158 or presented to one or more other relevant parties 168, such as medical staff at a hospital to which the patient is to be transported.

According to a first aspect, the present invention provides a method. FIG. 2 is a flowchart of an example of a method 200, which may be considered to be a method for determining action to be taken in response to an emergency call. The method 200 may comprise a computer-implemented method and, as such, may be performed using one or more processors. In some examples, the method 200 may be performed using a processor of a computing device, such as a smartphone in the possession of the patient 102. The patient may initiate an emergency call using such a smartphone or computing device or using a device such as an emergency call button connected to the smartphone or computing device. The method 200 comprises, at step 202, determining that an emergency call has been initiated. For example, if the emergency call is initiated using the smartphone, then initiating the emergency call may cause an application to be launched on the smartphone, or if the emergency call is initiated using an emergency call button, then this may cause an application to be launched on the smartphone or on another computing device.

At step 204, the method 200 comprises extracting, from speech transmitted as part of the emergency call, features indicative of a medical condition or event (i.e. a medical event) relating to a subject. A medical condition may be considered to refer to an illness, injury or disease affecting the subject, and a medical event may be considered to refer to an event that has affected the subject's health, such as a fall. As used herein, the "subject" may refer to the patient 102. In some embodiments, processing of the speech (i.e. audio data from the call) at step 202 may be performed after termination of the emergency call, or in stages while the emergency call is in progress, for example by processing one portion of the recorded call at a time. In other embodiments, however, processing may advantageously be performed in real time. Extracting features of from the speech may, in some examples, be performed using the speech processing module 114, by transcribing the speech and using word embedding techniques to identify common themes, words or phrases occurring during the emergency call. The words and phrases used during the emergency call may, for example, provide an indication of an injury, an illness or a disease relevant to the subject/patient 102. This may be explicit, for example if the patient indicates that they have fallen and cut their head, or may be implicit, for example if the patient indicates that they have suffered from a particular illness in the past and the symptoms being suffered, and mentioned during the call, indicate that the patient may be suffering from the illness again.

The method 200 comprises, at step 206, obtaining medical data relating to the subject. The medical data relating to the subject may be obtained from the patient's electronic health record, for example using the health record data extraction module 124. In some cases, specific data from the electronic health record may be extracted based on DICOM classifications used in the health record, or other labels or headings used to identify information (e.g. "patient name", "prescribed medication", "medical history" or the like).

The obtained medical data and the extracted features are then provided to a predictive model which is configured to determine the severity or seriousness of the situation or health of the patient 102, otherwise referred to as an acuity level. In its simplest sense, the predictive model may comprise a set of rules which can be used to estimate an acuity level based on times a particular word or phrase is used in the emergency call (i.e. the extracted features) and on particular items of information occurring in the patient's electronic health record (i.e. the medical data). In other examples, the predictive model may comprise one or more trained machine learning models. The predictive model is trained to use its inputs to determine the acuity level, for example. Thus, the method 200 comprises at step 208, predicting, based on the extracted features and the medical data, an acuity level of the subject.

At step 210, the method 200 comprises determining, based on the acuity level, an action to be taken in respect of the subject. The determining performed at step 210 may also be performed using a predictive model. Again, a relatively simple arrangement may make use of a set of rules for determining an action to be taken based on the determined acuity level while, in some embodiments, one or more trained machine learning models may be used to make the determination. Thus, at least one of predicting an acuity level of the subject (step 208) and determining an action to be taken in respect of the subject (step 210) may be performed using a trained predictive model.

The action to be taken in respect of the subject/patient 102 may depend on the information provided to the predictive model and also on the facilities (e.g. medical facilities and transportation options) available in the vicinity of the patient. In some embodiments, the action to be taken in respect of the subject may comprise at least one action selected from a group comprising: transporting the subject to an emergency department; providing self-care instructions to the subject without dispatching transportation; providing treatment of the subject at the scene; transporting the subject to an appropriate healthcare provider; referring the subject to an appropriate community service; and providing a specific treatment or transport protocol. In other examples, the action to be taken in respect of the subject may comprise at least one action selected from a group comprising: dispatching an ambulance to take the subject to an emergency care facility; dispatching an ambulance to take the subject to a non-emergency care facility; dispatching a non-emergency vehicle to the subject; and contacting a caregiver for the subject.

In some embodiments, the extracted features and the obtained medical data may also be taken into account in the determination made at step 210. As noted previously, the determination of the action to be taken may comprise a determination of whether or not to dispatch someone to attend the patient 102, a determination of who (e.g. an ambulance team, a non-emergency care worker, or a relative of the patient) is to be dispatched to attend the patient, a determination of whether the patient is to be transported to a medical facility and/or a determination of the medical facility to which the patient is to be transported. As used herein, the term "medical facility" is considered to refer to any location to which a subject may be taken during or following a medical event. For example, such a facility may comprise a hospital, a doctor's office, a community service facility, a pharmacy, or the like.

The method 200 comprises, at step 212, providing an indication of the determined action for presentation to a recipient. The indication may, for example, be provided by the display module 156, and the determined action may be presented using the user interface 158, for example to the emergency response dispatcher 110 and/or to other relevant parties 168. In other examples, the indication of the determined action and other information may be provided in some other way, via an audio signal, a video message or via a data channel (e.g. a chatbot or any human-machine interaction interface or a display module). In some examples, triaging information may be encoded as video or audio message which can be provided to an audio/video call receiver system.

FIG. 3 is a flowchart of a further example of a method 300. The method 300 may comprise steps of the method 200 discussed above, and may also be considered to be a computer-implemented method for determining an action to be taken in response to an emergency call.

According to the method 300, the step of determining an action to be taken (step 212), may comprise, at step 302, determining, at a first time, a first action to be taken in respect of the subject and, at step 304, determining, at a second time, later than the first time, a second action to be taken in respect of the subject. The determination of the first action may comprise a determination of whether or not to dispatch someone to attend the patient and/or a determination of who should be dispatched to attend the patient. The determination of the second action to be taken may comprise a determination of whether or not to transport the patient to a medical facility and/or which medical facility the patient should be transported to. Thus, according to some embodiments, the first action may comprise dispatching an emergency responder to attend the subject, and the second action may comprise transporting the subject to a medical facility. In some examples, determining the second action to be taken may comprise determining a medical facility to which the subject is to be transported.

In another example, the first action may be determined based on the information available during the emergency call or immediately after the emergency call has ended. If the determination of the first action results in a medical team being dispatched to the patient 102, then the medical team may assess the patient, update the patient's electronic health record with new, current vital signs measurements and additional information obtained from attending the patient. The determination of the second action may be made based on the additional information available once the medical team has attended the patient and assessed the situation. Thus, by determining a second action to be taken at a later time, or pertinent information may be available, enabling a more appropriate determination to be made.

According to some embodiments of the method 300, the step of determining an action to be taken (step 212) may comprise, at step 306, determining, at a third time, later than the second time, a third action to be taken in respect of the subject. For example, a first action taken in respect of the patient may be to dispatch an ambulance to the patient, and a second action to be taken may be to transport the patient to a non-emergency medical facility. Further assessments of the patient may be made while the patient is being transported in the ambulance and, on the basis of further information and vital signs measurements, the method 300 may determine that the acuity level of the patient 102 has increased and consequently, that the patient should be transported to an emergency medical facility. Thus, by providing additional information, the method may determine the most appropriate action to be taken, even if this changes over time as a result of changing conditions or a worsening of the patient's condition.

The method 300 comprises, at step 308, receiving sensor data relating to health measurements acquired in respect of the subject. Such sensor data may, for example, comprise data acquired using one or more medical sensors associated with patient 102, such as a heart rate sensor, a pulse oximeter, a blood pressure sensor, and the like. In some examples, as indicated above, the sensor data may comprise clinical data 170 acquired by medical professionals attending the patient, for example once an ambulance team has arrived at the patient's location. In examples where sensor data is available, then predicting an acuity level (step 208) of the subject and determining an action to be taken in respect of the subject may be based on the received sensor data. In this way, the determinations and recommendations made by the predictive model can be even more appropriate as they are based on the most up-to-date data available.

According to some embodiments, providing an indication of the determined action for presentation to a recipient (step 212) may comprise securely transmitting the indication of the determined action to the recipient, along with at least one of: data relating to the emergency call, the features extracted from the speech, at least a portion of the medical data relating to the subject, and the predicted acuity level. As indicated above, providing the indication of the determined action may be performed using the secure module 148, which may use various encryption techniques and/or blockchain technology. The amount of data to be presented along with the indication of the determined action may depend on the recipient of the information. For example, all of the information (i.e. the data relating to the emergency call, the features extracted from the speech, at least a portion of the medical data relating to the subject, and the predicted acuity level) may be provided to the emergency response dispatcher 110, while if the determined action is to dispatch a taxi to transport the patient 102 to a local doctors' surgery, then just the determined action and selected medical data (e.g. data identifying the patient) may be provided.

Figure 4:
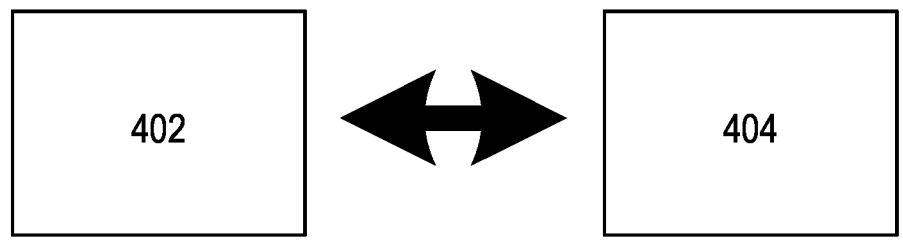
FIG. 4 is a schematic illustration of an example of a processor in communication with a computer-readable medium.

According to a second aspect, the present invention provides a computer program product. FIG. 4 is a schematic illustration of an example of a processor 402 in communication with a computer medium 404. According to various embodiments, a computer program product comprises a non-transitory computer-readable medium 404, the computer-readable medium having computer-readable code embodied therein, the computer-readable code being configured such that, on execution by a suitable computer or processor, the computer or processor is caused to perform the steps of the methods 200, 300 disclosed herein. The computer-readable medium 404 may, for example, comprise a medium located in a computing device (e.g. a smartphone) in the possession of or associated with the patient 102.

Figure 5:
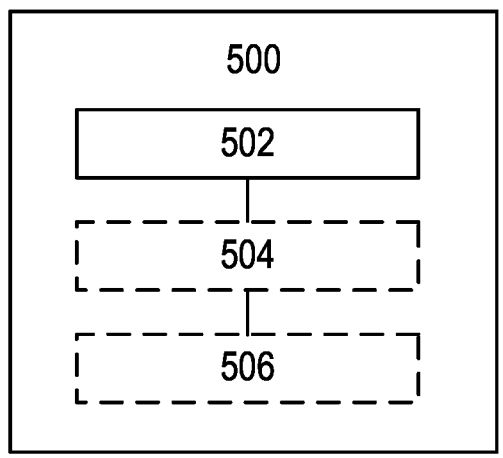
FIG. 5 is a schematic illustration of an example of an apparatus for responding to emergency calls.

According to third aspect, the present invention provides an apparatus. FIG. 5 is a schematic illustration of an example of an apparatus 500 for determining an action to be taken in response to an emergency call. The apparatus 500 comprises a processor 502 which may, in some examples, comprise or be similar to the processor 402 discussed above. For example, the processor 502 may be configured to perform one or more steps of the methods 200, 300 discussed herein, and may be configured to perform steps by executing instructions and/or computer-readable code. The processor 502 is configured to receive an indication that an emergency call has been initiated; extract, from speech transmitted as part of the emergency call, features indicative of a medical condition or event relating to a subject; obtain medical data relating to the subject; predict, based on the extracted features and the medical data, an acuity level of the subject; determine, based on the acuity level, an action to be taken in respect of the subject; and provide an indication of the determined action for presentation to a recipient. In some embodiments, the apparatus 500 may comprise a computing device such as a desktop computer, a laptop computer, a tablet computer, a smartphone, a wearable device (e.g. a smartwatch), or the like.

As discussed above, the processor 502 of the apparatus 500 may perform the above functions once an emergency call has been initiated using a separate device, such as an emergency call button. In other embodiments, the emergency call may be made using the apparatus 500 itself. Thus, in some embodiments, the apparatus 500 may further comprise a call initiation unit 504 for enabling an emergency call between a caller and a call receiver to be initiated. The call initiation unit 504 may comprise a button which, when pressed or activated, enables communication between the caller (e.g. the patient 102) and the call receiver (e.g. the emergency response dispatcher 110). In other examples, the call initiation unit 504 may comprise various components of a smartphone or computing device that enable the emergency call to be initiated.

In some embodiments, the apparatus 500 may further comprise a memory 506 configured to store at least one of: a health record relating to the subject; a predictive model for predicting the acuity level; a predictive model for determining an action to be taken in respect of the subject; and a predictive model for predicting the acuity level and for determining an action to be taken in respect of the subject. This and other content may be stored in and/or retrieved from the memory 506 for example by the processor 502. For example, when vital signs measurements are available, ease may be added to the patient's electronic health record and stored in the memory 506. Similarly, when the processor 502 is to obtain a medical data relating to the subject, this data may be extracted from the electronic health record stored in the memory 506. By handling all processing locally using the processor 502 of the device 500, and accessing data from a local memory 506, it provides improved security (no personal data transferred initially, and it is not necessary to retrieve personal data relating to the patient 102 from an external source), the processing may be done quicker as the processing is performed using the processor 502 of the apparatus 500, and as long as a communication link can be established between the caller (e.g. the patient 102) and the call receiver (e.g. the emergency response dispatcher 110), for example over a standard phone line, then the processing can be performed without internet signal.

Figure 6:
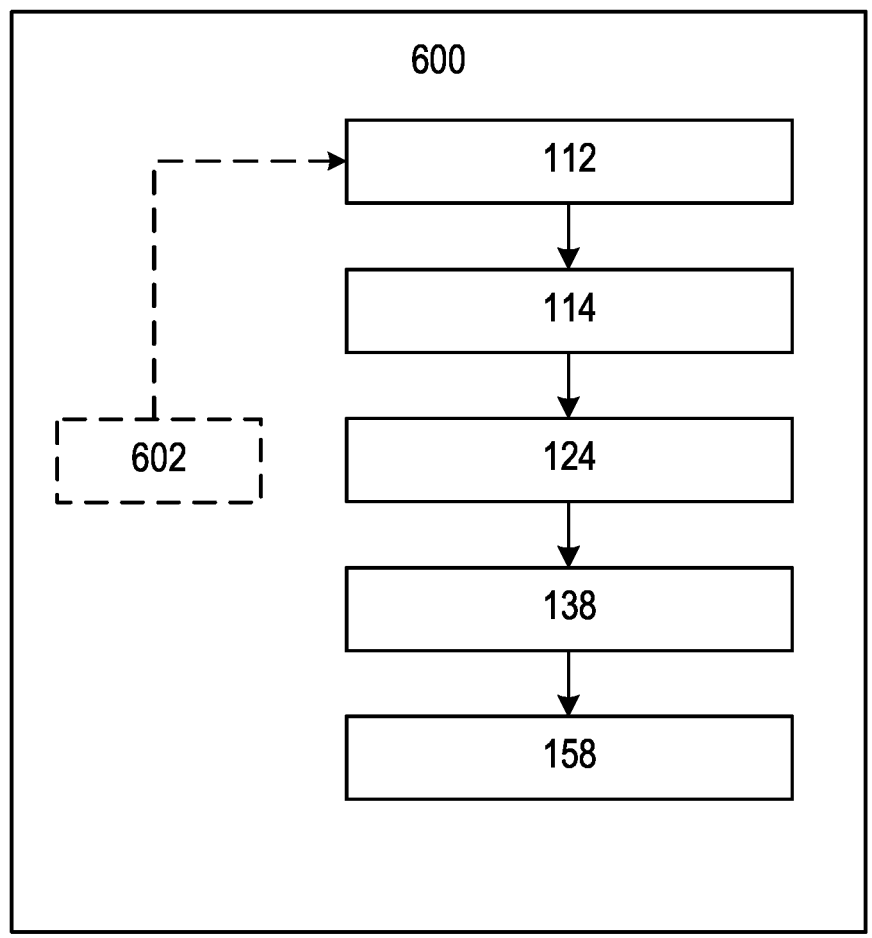
FIG. 6 is a schematic illustration of an example of a system for responding to emergency calls.

According to a fourth aspect, a system is provided. FIG. 6 is a schematic illustration of an example of a system 600 for determining an action to be taken in response to an emergency call. The system 600 comprises a call detection module 112 for detecting the initiation of an emergency call; a speech processing module 114 for extracting, from speech transmitted as part of the emergency call, features indicative of a medical condition or event relating to a subject; an extraction module 124 for extracting, from a memory, medical data relating to the subject; at least one prediction module 138 for predicting, based on the extracted features and the medical data, an acuity level of the subject; and determining, based on the acuity level, an action to be taken in respect of the subject; and a user interface 158 for presenting an indication of the determined action. The various components of the system 600 may be contained within a single device, such as the apparatus 500, or distributed among multiple devices capable of communicating with one another.

In some embodiments, the system 600 may further comprise a call initiation module 602 for enabling the emergency call to be initiated. In examples where the call initiation module 602 does not form part of the same apparatus (e.g. the apparatus 500) used to perform the processing (i.e. the steps of the methods 200, 300), the call initiation module may be connected via a wired or wireless connection with other components of the system 600.

Embodiments of the present disclosure provide a mechanism by which triaging of a patient making an emergency call can be carried out automatically, making use of information from multiple sources, in order to make an informed and appropriate decision regarding the action to be taken in respect of the patient. Moreover, the triaging process may be repeated once more information (e.g. vital signs measurements) becomes available, and to take account of any changes in the situation, to ensure that the decision regarding the action to be taken is the most appropriate one in the circumstances. This not only contributes to the best outcome for the patient, but also reduces the burden put on human emergency call handlers, reduces the risk of an inappropriate decision being made as a result of human error, and ensures that emergency response resources are used only for those cases where they are most needed.

Example

In order to test the systems and methods discussed herein a data set consisting of more than 3,600 recorded calls was used. The calls were made using a Personal Emergency Response System (PERS), which includes a pendant with a help button which a person (e.g. an elderly or vulnerable person) can press in case of an incident, such as a fall, breathing problems or some other emergency situation. The person is connected to a trained agent in the PERS response centre, who ensures the appropriate help is provided to the user (e.g. no help needed, dispatch of an informal responder, dispatch of an ambulance). The recorded calls were transcribed using automated speech recognition (ASR) software. Of these calls, 63% were made in respect of actual incidents (versus 37% test or accidental calls) where help was sent to the home. In 46% of the calls relating to incidents, the help included dispatching an ambulance to the home.

A combination of natural language processing and a predictive model (i.e. advanced machine learning) was applied to the transcribed calls to make a prediction regarding whether or not the call is considered to relate to an incident, and if so, whether or not it would be appropriate to dispatch an ambulance to the home of the caller. A development and test set (75:25%) were used, and to avoid overfitting it was ensured that all the calls for one individual were included in either the development or test set. Results of the test set are shown in Table 1 below.

TABLE 1

| Prediction target | AUC score | Most indicative words |
|---|---|---|
| Incident | 87% | Door, please, ambulance |
| Incident with Ambulance dispatch | 76% | Hospital, dispatch, medical |

The results in Table 1 indicate that the predictive model is able to correctly predict that a call was classified as an incident 87% of the time, with the terms "door", "please" and "ambulance" occurring most frequently in those calls. Furthermore, the predictive model is able to correctly predict that a call was classified as an incident requiring dispatch of an ambulance 76% of the time, with the terms "hospital", "dispatch" and "medical" occurring most frequently in those calls. An area under the curve (AUC) discriminatory accuracy of 76-87% shows that call-based prediction of acuity level is effective.

Training the Predictive Model

A predictive model was trained to determine action to be taken (i.e. a decision regarding emergency transport of the patient 102, and a decision regarding the patient's attendance at a medical facility, referred to as "emergency outpatient visits") based on data from a Personal Emergency Response System (PERS) and data from electronic health records (EHRs).

Variables from the PERS data that were evaluated for inclusion in the predictive models included subscriber demographics, self-reported medical conditions, information about the caregiver network, and other variables associated with the PERS call-center. These variables included the type, frequency and outcome of prior incidents and accidental emergency calls, as well as the time since the most recent incident or accidental call, also referred to as 'recency'. From the EHR data, predictor variables included the frequency and recency of (emergency) outpatient encounter and inpatient admissions, the length-of-stay of past admissions, as well as the 50 most frequently occurring primary diagnoses for outpatient visits and inpatient admissions. Up to two years' worth of retrospective PERS and EHR data were used to construct the features.

The predictive models were developed using a boosted regression trees approach called extreme gradient boosting with the statistical software, using a tree-based booster. Initially, 211 predictors (i.e. features) derived from the linked PERS and EHR data were considered. Only predictors that were statistically significantly different between the group of patients with and without the outcome in the model development cohort were selected for inclusion into the gradient boosting method.

The five most important variables for the emergency hospital transport predictive model were all derived from PERS data (see Table 2 below). For the models of emergency outpatient visits and the combined endpoint, there was a mix of EHR and PERS variables. For all predictive models, previous recent emergency encounters are among the most important variables. The average of the five most important variables in the predictive models and their respective values in the groups with and without the outcome as shown in Table 2 below. Values are reported for the model development cohort.

TABLE 2

| Rank | Source | Feature | Value in patients with outcome | Value in patients without outcome | p-value |
|---|---|---|---|---|---|
| | | Emergency hospital transport in 1 year | | | |
| 1 | PERS | Sum of incidents | 2.6 ± 4.1 | 0.5 ± 1.6 | <0.001 |
| 2 | PERS | Recency of incidents | 391 ± 301 days | 612 ± 230 days | <0.001 |
| 3 | PERS | Sum of calls where user does not need help | 19.1 ± 12.4 | 16.4 ± 12.2 | 0.005 |
| 4 | PERS | Recency of accidental calls | 363 ± 288 days | 424 ± 291 days | 0.008 |
| 5 | PERS | Recency of incidents with EMS assistance, no hospital transport | 595 ± 245 days | 696 ± 130 days | <0.001 |
| | | Emergency outpatient visit in 1 year | | | |
| 1 | EHR | Recency of emergency outpatient visits | 386 ± 279 days | 626 ± 212 days | <0.001 |
| 2 | EHR | Recency of outpatient visits | 77 ± 137 days | 353 ± 324 days | <0.001 |
| 3 | EHR | Sum of emergency outpatient visits | 25.9 ± 23.8 | 11.9 ± 18.4 | <0.001 |
| 4 | PERS | Recency of calls where user does not need help | 94 ± 190 days | 67 ± 135 days | 0.048 |
| 5 | PERS | Age at PERS enrollment | 74 ± 13 | 77 ± 12 | 0.006 |

The processor 402, 502 referred to herein can comprise one or more processors, processing units, multi-core processors or modules that are configured or programmed to control the apparatus 500 in the manner described herein. In particular implementations, the processor 402, 502 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for determining an action to be taken in response to an emergency call, the apparatus comprising:
   a processor configured to:
      receive an indication that an emergency call has been initiated;
      extract, from speech transmitted as part of the emergency call, features indicative of a medical condition or event relating to a subject;
      obtain medical data relating to the subject;
      predict, based on the extracted features and the medical data, an acuity level of the subject;
      determine, based on the acuity level, an action to be taken in respect of the subject; and
      provide an indication of the determined action for presentation to a recipient,
         wherein providing the indication of the determined action for presentation to the recipient comprises securely transmitting the indication of the determined action to the recipient, along with at least one of: data relating to the emergency call, the features extracted from the speech, at least a portion of the medical data relating to the subject, and the predicted acuity level, and
         wherein a level of detail and amount of information in the indication of the determined action is tailored, using the extraction model, based on one or more characteristics associated with the recipient.

2. An apparatus according to claim 1, further comprising:
   a call initiation unit for enabling an emergency call between a caller and a call receiver to be initiated.

3. An apparatus according to claim 1, further comprising:
   a memory configured to store at least one of: a health record relating to the subject; a predictive model for predicting the acuity level; a predictive model for determining an action to be taken in respect of the subject; and a predictive model for predicting the acuity level and for determining an action to be taken in respect of the subject.

4. A computer-implemented method for determining an action to be taken in response to an emergency call, the method comprising:
   determining that an emergency call has been initiated;
   extracting, from speech transmitted as part of the emergency call, features indicative of a medical condition or event relating to a subject;
   obtaining medical data relating to the subject;
   predicting, based on the extracted features and the medical data, an acuity level of the subject;
   determining, based on the acuity level, an action to be taken in respect of the subject; and
   providing an indication of the determined action for presentation to a recipient,
      wherein providing the indication of the determined action for presentation to the recipient comprises securely transmitting the indication of the determined action to the recipient, along with at least one of: data relating to the emergency call, the features extracted from the speech, at least a portion of the medical data relating to the subject, and the predicted acuity level, and
      wherein a level of detail and amount of information in the indication of the determined action is tailored, using the extraction model, based on one or more characteristics associated with the recipient.

5. A computer-implemented method according to claim 4, wherein determining an action to be taken comprises:
   determining, at a first time, a first action to be taken in respect of the subject; and
   determining, at a second time, later than the first time, a second action to be taken in respect of the subject.

6. A computer-implemented method according to claim 5, wherein the first action comprises dispatching an emergency responder to attend the subject; and wherein the second action comprises transporting the subject to a medical facility.

7. A computer-implemented method according to claim 5, wherein determining the second action to be taken comprises determining a medical facility to which the subject is to be transported.

8. A computer-implemented method according to claim 5, wherein determining an action to be taken comprises:
   determining, at a third time, later than the second time, a third action to be taken in respect of the subject.

9. A computer-implemented method according to claim 4, further comprising:
   receiving sensor data relating to health measurements acquired in respect of the subject;
   wherein said predicting an acuity level of the subject and determining an action to be taken in respect of the subject are based on the received sensor data.

10. A computer-implemented method according to claim 4, wherein providing an indication of the determined action for presentation to a recipient comprises securely transmitting the indication of the determined action to the recipient, along with at least one of: data relating to the emergency call, the features extracted from the speech, at least a portion of the medical data relating to the subject, and the predicted acuity level.

11. A computer-implemented method according to claim 4, wherein at least one of predicting an acuity level of the subject and determining an action to be taken in respect of the subject are performed using a trained predictive model.

12. A computer-implemented method according to claim 4, wherein the action to be taken in respect of the subject comprises at least one action selected from a group comprising: transporting the subject to an emergency department; providing self-care instructions to the subject without dispatching transportation; providing treatment of the subject at the scene; transporting the subject to an appropriate healthcare provider; referring the subject to an appropriate community service; providing a specific treatment or transport protocol; dispatching an ambulance to take the subject to an emergency care facility; dispatching an ambulance to take the subject to a non-emergency care facility; dispatching a non-emergency vehicle to the subject; and contacting a caregiver for the subject.

13. A computer program product comprising a non-transitory computer-readable medium, the computer-readable medium having computer-readable code embodied therein, the computer-readable code being configured such that, on execution by a suitable computer or processor, the computer or processor is caused to perform the method of claim 4.

14. A system for determining an action to be taken in response to an emergency call, the system comprising:
   a call detection module for detecting the initiation of an emergency call;
   a speech processing module for extracting, from speech transmitted as part of the emergency call, features indicative of a medical condition or event relating to a subject;
   an extraction module for extracting, from a memory, medical data relating to the subject;
   at least one prediction module for:
      predicting, based on the extracted features and the medical data, an acuity level of the subject; and
      determining, based on the acuity level, an action to be taken in respect of the subject; and
   a user interface for presenting an indication of the determined action,
      wherein the indication of the determined action comprises securely transmitting the indication of the determined action to a recipient, along with at least one of: data relating to the emergency call, the features extracted from the speech, at least a portion of the medical data relating to the subject, and the predicted acuity level, and
      wherein a level of detail and amount of information in the indication of the determined action is tailored, using the extraction model, based on one or more characteristics associated with the recipient.

15. A system according to claim 14, further comprising:
a call initiation module for enabling the emergency call to be initiated.

* * * * *